United States Patent [19]
Lentini et al.

[11] Patent Number: 5,942,212
[45] Date of Patent: Aug. 24, 1999

[54] SELF TANNING COMPOSITION CONTAINING DHA AND α HYDROXY ACIDS

[75] Inventors: Peter J. Lentini, Bayside; Paul Tchinnis, Copiague; Neelam Muizzuddin, Bethpage, all of N.Y.

[73] Assignee: E-L Management Corp., New York, N.Y.

[21] Appl. No.: 08/859,872

[22] Filed: May 21, 1997

Related U.S. Application Data

[63] Continuation-in-part of application No. 08/753,021, Nov. 19, 1996.
[51] Int. Cl.$^6$ ....................................................... A61K 7/42
[52] U.S. Cl. ............................ 424/59; 514/558; 514/675
[58] Field of Search ..................................... 514/558, 675; 424/59

[56] References Cited

U.S. PATENT DOCUMENTS 5,091,171  2/1992  Yu et al. .................................. 424/642

OTHER PUBLICATIONS

Sargisson, S., Growth in Skin Care Products Sale is Atiributable to α–Hydroxyacids (AHA's) at Least 200 New AHA Products Introduced in 1994., Drug & Cosmetic Industry, v 156, N3, p. 34+, Mar. 1995.

Women's Wear Daily, "Lauder's Acid Tan Will Expand Self–Action Line by Introducing Super Tan," Feb. 18, 1994, p. 5.

*Primary Examiner*—Jose' G. Dees
*Assistant Examiner*—Michael A. Williamson
*Attorney, Agent, or Firm*—Karen A. Lowney, Esq.

[57] ABSTRACT

The present invention relates to a self-tanning composition comprising an effective amount of DHA in combination with an effective amount of a long-chain alpha hydroxy acid (AHA). In a preferred embodiment, the AHA is α-hydroxy lauric acid.

18 Claims, No Drawings

SELF TANNING COMPOSITION CONTAINING DHA AND α HYDROXY ACIDS

RELATED APPLICATIONS

This application is a continuation-in-part of co-pending application Ser. No. 08/753,021, filed Nov. 19, 1996 the contents of which are incorporated herein by reference.

FIELD OF THE INVENTION

The present invention relates to self-tanning agents. More specifically, the invention relates to DHA-containing self-tanning agents with improved color development and longevity.

BACKGROUND OF THE INVENTION

Compositions useful for inducing a tan on the human epidermis without the assistance of exposure to the sun have been known for many years. For example, U.S. Pat. No. 2,949,403 discloses that the compound dihydroxyacetone (DHA) can be used for this purpose; Since that report, DHA has been widely employed in commercial self-tanners. Many variations on the basic DHA formulation have been proposed to overcome or bolster some of the inherent inadequacies observed when using DHA alone as the active agent in a formulation. For example, DHA tends to impart an unpleasant orange cast to the skin of fair-skinned individuals; to compensate for this deficiency, various dyes have been incorporated with DHA(U.S. Pat. No. 4,708,865). Moreover, DHA has also been incorporated into formulations with sunscreens, such as octyl methyl PABA(e.g., U.S. Pat. Nos. 4,434,154 and 3,177,120).

Additional difficulties arise with the formulation of DHA for efficient application to the skin. DHA is understood to work by reacting with skin proteins and amino acids to elicit the skin-coloring effect. Standard formulations of DHA are usually creams or lotions from which the DHA must diffuse from the base into the skin to effect the color change. The usual excipients used in these formulations, e.g., emulsifiers, oils, waxes, and the like, frequently trap a portion of the DHA in a surface film on top of the skin, thereby reducing its ability to penetrate the epidermis properly, where it must be located to accomplish the desired effect. The failure to penetrate results in a loss of depth and longevity of the artificial tan.

As the evidence accumulates as to the damaging effects of prolonged exposure to the sun, the importance of self-tanners has grown concurrently. As the demand for self-tanners has increased, however, so has consumer demand for a tanner which has a natural looking color, and which produces a longer lasting tan. Therefore, there continues to be a need for a self-tanning composition which meets these criteria. The present invention now satisfies these consumer needs.

SUMMARY OF THE INVENTION

The present invention relates to a self tanning composition comprising a self-tanning effective amount of DHA in combination with an effective amount of a long-chain alpha-hydroxy acid(AHA). The compositions of the present invention have been found to produce a tan that remarkably similar to a naturally produced tan, and also yields a tan that lasts longer than the tan induced by various known self-tanning products. The combination of DHA with the long chain AHA also appears to result in a rapid penetration of the active ingredient into the skin, thereby resulting in a more rapid onset of the tan, in addition to this enhanced appearance and longevity.

The invention also relates to a method for producing an artificial tan on the skin comprising applying to the skin a composition comprising a self-tanning effective amount of DHA in combination with an effective amount of a long-chain AHA. The invention also relates to a method of enhancing the self-tanning efficacy of DHA by combining DHA with an effective amount of a long chain AHA.

DETAILED DESCRIPTION OF THE INVENTION

Alpha hydroxy acids(AHAs), more specifically identified as 2-hydroxycarboxylic acids, generally are defined by the following formula:

$$(R_1)(R_2)C(OH)COOH$$

wherein $R_1$ and $R_2$ may be the same or different, and are selected from the group consisting of H, F, C, Br, alkyl, aralkyl, or aryl having 1–29 carbon atoms. The alkyl, aryl or aralkyl groups may be straight, branched or cyclic, and further $R_1$ and $R_2$ may be substituted with OH, CHO, COOH or a $C_{1-9}$ alkoxy group. α-Hydroxycarboxylic acids have been used to treat ichthyosis, hyperkeratoses, dandruff and acne (see, U.S. Pat. Nos. 3,879,537 to Van Scott et al.; 3,920,835, 3,988,470, and 4,234,599 to Van Scott et al.; 3,984,566 to Van Scott et al.; and 4,105,782 to Yu et al.; respectively). α-Hydroxycarboxylic acids have also been used to treat dry skin (see, U.S. Pat. Nos. 4,105,783 to Yu et al.; 4,194,007 to Van Scott et al.; 4,197,316 to Yu et al.; 4,380,549 to Van Scott et al.; 4,363,815 to Yu et al. and 4,091,171 to Yu et al. α-Hydroxycarboxylic acids have also been used to enhance the antiinflammatory action of corticosteroids (see, U.S. Pat. No. 4,246,261 to Van Scott et al.). U.S. Pat. No. 5,254,343 to Parah et el. discloses the use of salts of α-hydroxyacids in conjunction with steroids to minimize cutaneous atrophy, a side-effect of steroid application to the skin. Certain of these compounds have been widely used in the cosmetics industry as pH adjusters. In addition, in high concentration, certain α-hydroxyacids have been used by dermatologists as the active component in chemical peels.

In the present invention, long chain AHAs, namely, $C_6$–$C_{22}$ AHAs, preferably alkyl AHAs, are used to unexpectedly enhance the skin-tanning properties of DHA in self-tanning compositions. In a preferred embodiment, the AHA is a $C_8$–$C_{18}$ AHA, preferably α-hydroxy octanoic, α-hydroxy decanoic or α-hydroxy lauric acid, and most preferably, the AHA is a $C_{12}$ AHA, more specifically α-hydroxy lauric acid.

In the formulations of the present invention, one or more long chain AHAs are used in an total amount of from about 0.01–20%, more preferably from about 0.5–10%, most preferably from about 1–5%, by weight of the total composition. The AHA can be combined with a typical self-tanning formulation of any type in which DHA is the principle self-tanning active. In a typical self-tanning formulation, DHA is present in an amount of from about 2.5 to about 10% by weight of the total formulation. The vehicle may be any cosmetically or pharmaceutically acceptable vehicle, and in any form appropriate for topical application. Examples of the forms in which the self-tanning agent can be applied are creams, lotions, or sprays. If the vehicle to be used is an emulsion, it is preferred that the formulation contains a high molecular weight cationic polymer, which aids in thickening the vehicle and also assists in stabilizing the active components. In particular, the polymer used is of the type described in U.S. Pat. Nos. 5,100,660; 4,849,484; 4,835,206; 4,628,078; 4,599,379; and EP 228,868; the contents of each of these documents is incorporated herein by reference. A particularly preferred polymer for use in the present invention is commercially available from Allied Colloids under the name of Salcare SC96, which is a homopolymer of dimethylaminoethylmethacrylate(Polyquaternium 37) dispersed in propylene glycol dicaprylate dicaprate and PPG-1 trideceth-6.

Various other optional ingredients may be included in the compositions of the present invention, these include but are not limited to perfumes, preservatives, emollients, antiseptics, pigments, dyes, humectants, propellants, as well as other classes of materials whose presence may be cosmetically, medicinally or otherwise desirable. Common examples can be found in the CTFA International Cosmetic Ingredient Dictionary 4th Edition, The Cosmetic, Toiletry, and Fragrance Association, Inc., Washington, D.C., 1991. Common examples of such ingredients are provided below by way of example and not limitation.

The formulations of the present invention provide a significant improvement over currently available self-tanning products. Short chain AHAs, such as lactic acid, have been previously used in self-tanning products, but such acids are known to be irritating to the user. A particularly favorable pH for activity of DHA is about 3.5–4. While not wishing to be bound by any particular theory, it is believed that the acid pH facilitates penetration of DHA and interaction of the DHA with amino acids in the skin. However, achieving this optimum environment has been historically difficult, both because of resultant irritation, and also because of the resulting instability of DHA. Unlike lactic acid, however, the longer chain AHAs are non-irritating, while at the same time providing an unexpected enhancement of the effect of DHA by producing a rapidly appearing, deep color, which can last at least about 3 days, more preferably as long as 5 days, and most preferably as long as 7 days at higher levels of DHA. In addition, the color produced is very natural in appearance. While a number of the non-irritating longer chain AHAs provide a rapid onset and deep color self-tan, a particularly beneficial result is achieved in the combination of α-hydroxy lauric acid and DHA. In a preferred embodiment, to achieve a long-lasting, dark tan, the composition comprises α-hydroxy lauric acid in an amount of from about 0.5–2% and DHA in an amount of from about 5–9%. A particularly desirable effect is achieved when the ratio of DHA to α-hydroxylauric acid is approximately 9:1.5.

The invention will be further illustrated by the following non-limiting examples:

EXAMPLE 1

Several organic acids are tested for their ability to produce a rapid, deep tan in combination with DHA. In the following experiments, each formulation contains an equivalent concentration of acid in combination with the same amount of DHA. Each combination is applied to the skin of panelists (twelve groups of seven panelists each) in an amount of 800 μl on one arm, and an equal amount of control product containing only DHA and no acid on the other arm. Color measurements are taken with a Chromameter before treatment and after, at 30 minutes, 1 hour, 2 hours, 5 hours and 24 hours. Decrease in reflectance and increase in red coloration and yellow coloration ($\Delta L^*$, $\Delta a^*$, and $\Delta b^*$) are calculated as compared to baseline skin color, to determine $\Delta E^*$, expressing total change in color. $\Delta E^*$ is calculated as $\Delta E^*$=the square root of $[(\Delta L^*)^2+(\Delta a^*)^2+(\Delta b^*)^2]$. The results observed, showing total change of color, are shown in Table 1.

TABLE 1

| Product | 30 min. | 1 hour | 2 hours | 5 hours | 24 hours |
|---|---|---|---|---|---|
| Control | 1.48 | 1.95 | 2.78 | 4.21 | 5.06 |
| α-OH octanoic | 1.9 | 2.58 | 2.93 | 5.34 | 5.82 |
| α-OH decanoic | 1.70 | 1.98 | 2.79 | 4.88 | 6.21 |
| 2-OH palmitic | 1.38 | 1.79 | 2.78 | 3.95 | 4.71 |
| 2-OH lauric | 1.54 | 2.81 | 3.73 | 4.66 | 5.63 |
| 2-OH stearic | 1.88 | 1.61 | 2.61 | 4.23 | 5.30 |
| α-OH sebasic | 0.93 | 1.39 | 2.51 | 4.23 | 5.35 |
| lactic acid | 1.33 | 3.19 | 3.31 | 4.48 | 4.91 |
| salicylic acid | 1.22 | 1.6 | 2.97 | 4.64 | 4.82 |
| tartaric acid | 1.05 | 1.53 | 2.13 | 4.56 | 4.64 |
| citric acid | 1.39 | 1.61 | 2.17 | 3.94 | 5.12 |
| Actiplexx 1177* | 1.76 | 2.42 | 2.77 | 4.33 | 4.64 |
| Actiplexx 1072** | 1.80 | 1.69 | 2.72 | 4.39 | 4.63 |

*Mixture of glycolic, lactic, citric and ascorbic acids
**Mixture of salicylic and lactic acids The results show rapid onset of tan and good color within one hour of treatment with α-hydroxy octanoic, α-hydroxy decanoic and α-hydroxy lauric acids.

EXAMPLE 2

The effect of a long-chain α-hydroxy acid on enhancing self-tanning is compared with that of certain inorganic acids. Specifically, a composition of the invention, containing a standard base formulation with 9% DHA and 1.5% α-hydroxy lauric acid(I), pH 3.11, is compared with an identical base containing 9% DHA and 0.3% of a 1N solution of hydrochloric acid(II), pH 2.52, and a second identical base containing 0.3% phosphoric acid(III), pH 2.01. A sample containing 9% DHA and 0.5% lactic acid (IV)(88%) is also included in the evaluation. The concentrations of the comparison acids are selected so as to confer a final pH of between 2.1 and 3.1 on all test samples. A total of twenty-four panelists take part in the study. The panel is divided in three groups of 7–8 each, corresponding to the three groups of non-long chain α-hydroxyacid containing compositions. The panelists apply the composition of the invention as the control on one arm, and one of the other formulations on the other, in an amount of about 1000 μl each, and blend in the products. Color measurements are obtained as described above, before treatment and after 5 hours and 24 hours.

All products demonstrate a decrease in skin reflectance and an increase in skin redness and yellow coloration, due to the tanning effect of the DHA. Table 2 shows the specific results, in terms of $\Delta E^*$(total color change) obtained with each product tested.

TABLE 2

|  | I | II | III | IV |
|---|---|---|---|---|
| 5 hours | 6.10 | 5.82 | 4.78 | 5.28 |
| 24 hours | 7.71 | 7.16 | 6.88 | 6.25 |

The results show that, although all acid products exhibit good self-tanning properties, the tan produced by the composition of the invention produces the darkest color.

EXAMPLE 3

Compositions of the present invention are compared with other commercially available self-tanners which do not contain a long-chain AHA, with respect to darkness of tan and length of time the tan lasts. A total of forty-six panelists are divided into six groups of 7 to 9 each, corresponding to six test products. The products to be tested are as follows:

A. Estée Lauder Supertan Medium(Control)containing 1% lactic acid and 5% DHA.

B. Estée Lauder Supertan Dark containing 1.2% lactic acid and 7% DHA.

C. Composition of the invention containing 9% DHA and 1.5% α-hydroxy lauric acid.

D. Composition of the invention containing 7% DHA and 0.5% α-hydroxy lauric acid.

E. Composition of the invention containing 5% DHA and 0.5% α-hydroxy lauric acid.

F. Commercial Self-Tanner "I".

G. Commercial Self Tanner "II".

The panelists apply the control on one arm and one of the other formulations on the other. About 750 μl of each product is applied and blended in until absorbed. Color measurements are obtained with the Chromameter before treatment and after 1 hour, 2 hours, 5 hours, 24 hours, 3 days, 7 days and 9 days. Decrease in reflectance and increase in red coloration and yellow coloration obtained from the Chromameter are calculated as compared to baseline skin color, and total color change $\Delta E^*$ is calculated for each time point. The results of the study are presented in Table 3; the letters identifying test products are as defined above.

TABLE 3

|  | A | B | C | D | E | F | G |
|---|---|---|---|---|---|---|---|
| 1 hour | 1.37 | 1.29 | 1.57 | 1.63 | 1.15 | 1.31 | 1.53 |
| 2 hours | 1.90 | 2.41 | 3.94 | 3.32 | 1.93 | 1.99 | 1.91 |
| 5 hours | 4.15 | 5.32 | 8.61 | 5.25 | 4.59 | 4.20 | 6.78 |
| 24 hours | 4.39 | 5.08 | 10.28 | 6.57 | 5.77 | 3.50 | 5.88 |
| 3 days | 1.13 | 1.93 | 2.83 | 2.71 | 1.29 | 1.27 | 1.40 |
| 7 days | 0.96 | 1.62 | 2.02 | 2.52 | 0.89 | 0.84 | 0.64 |
| 9 days | 0.86 | 1.10 | 0.71 | 1.26 | 0.39 | 0.62 | 0.54 |

As the table clearly shows, the products of the present invention, particularly C and D, show a deeper and longer lasting natural color than other commercially available products.

EXAMPLE 3

A self-tanning composition is prepared with the following components:

| Product | Wt. % |
|---|---|
| α-hydroxy lauric acid | 1.5 |
| purified water | QS |
| dihydroxyacetone | 9.0 |
| cyclomethicone | 25.0 |
| Polyquaternium-37/propylene glycol dicaprylate-dicaprate/PPG-1 trideceth 6 | 5.0 |

What we claim is:

1. A self tanning composition comprising an self-tanning effective amount of DHA in combination with an enhancing effective amount $C_8$–$C_{18}$ alkyl α-hydroxy acid.

2. The composition of claim 1 in which the acid is a $C_{12}$ acid.

3. The composition of claim 1 in which DHA is present in an amount of from about 2.5–10% by weight.

4. The composition of claim 1 in which the α-hydroxy acid is present in an amount of from about 0.1–20% by weight.

5. The composition of claim 4 in which the acid is α-hydroxy lauric acid.

6. The composition of claim 1 which comprises DHA in an amount of from about 2.5–10%, and α-hydroxy lauric acid in an amount of from about 0.1–20%.

7. The composition of claim 6 which comprises from about 5–10% DHA, and from about 1–5% α-hydroxy lauric acid.

8. The composition of claim 7 which comprises about 9% DHA and about 1.5% α-hydroxy lauric acid.

9. A method for enhancing the self-tanning effect of DHA which comprises combining a self-tanning effective amount of DHA with an enhancing effective amount of a $C_8$–$C_{18}$ alkyl α-hydroxy acid.

10. The method of claim 9 wherein the DHA is combined with the α-hydroxy acid in composition comprising DHA in an amount of from about 2.5–10%, and the α-hydroxy acid in an amount of from about 0.1–20%.

11. The method of claim 10 wherein the α-hydroxy acid is α-hydroxy lauric acid.

12. The method of claim 10 wherein the composition comprises from about 5–10% DHA, and from about 1–5% α-hydroxy lauric acid.

13. The method of claim 10 wherein the composition comprises about 9% DHA and about 1.5% α-hydroxy lauric acid.

14. A method of self-tanning which comprises applying to the skin a self-tanning effective amount of DHA with an enhancing effective amount of a $C_8$–$C_{18}$ alkyl α-hydroxy acid.

15. The method of claim 14 which comprises applying a composition comprising DHA in an amount of from about 2.5–10%, and the α-hydroxy acid in an amount of from about 0.1–20%.

16. The method of claim 14 wherein the α-hydroxy acid is α-hydroxy lauric acid.

17. The method of claim 14 wherein the composition comprises from about 5–10% DHA, and from about 1–5% α-hydroxy lauric acid.

18. The method of claim 14 wherein the composition comprises about 9% DHA and about 1.5% α-hydroxy lauric acid.

* * * * *